US006969530B1

(12) United States Patent
Curtis et al.

(10) Patent No.: US 6,969,530 B1
(45) Date of Patent: *Nov. 29, 2005

(54) MICROCAPSULES AND EMULSIONS CONTAINING LOW BLOOM GELATIN AND METHODS OF MAKING AND USING THEREOF

(75) Inventors: Jonathan Michael Curtis, Halifax (CA); Wei Zhang, Halifax (CA); Yulai Jin, Halifax (CA)

(73) Assignee: Ocean Nutrition Canada Ltd., Dartmouth (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/040,820

(22) Filed: Jan. 21, 2005

(51) Int. Cl.$^7$ .......... A61K 9/14; B32B 15/02; B01J 13/02
(52) U.S. Cl. .......... 424/489; 264/4.1; 264/4.3; 264/4.32; 264/4.33; 264/4.4; 264/4.7; 428/402.21; 428/402.24; 428/403; 424/494; 424/496; 424/497; 424/498
(58) Field of Search .......... 264/4.1, 4.3, 4.32, 264/4.33, 4.4, 4.7; 428/402.21, 402.24, 403, 428/489, 494, 496, 497, 498

(56) References Cited

U.S. PATENT DOCUMENTS

| 2,800,457 | A | 7/1957 | Green et al. .......... 428/402.2 |
| 4,217,370 | A | 8/1980 | Rawlings et al. .......... 426/98 |
| 4,219,439 | A | 8/1980 | Miyake et al. .......... 264/4.4 |
| 4,222,891 | A | 9/1980 | Okimoto et al. .......... 264/4.4 |
| 4,695,466 | A | 9/1987 | Morishita et al. |
| 4,744,933 | A | 5/1988 | Rha et al. |
| 4,749,620 | A | 6/1988 | Rha et al. |
| 4,861,627 | A | 8/1989 | Mathiowitz et al. |
| 4,895,725 | A | 1/1990 | Kantor et al. .......... 424/455 |
| 5,051,304 | A | 9/1991 | David et al. |
| 5,059,622 | A | 10/1991 | Sears .......... 514/549 |
| 5,204,029 | A | 4/1993 | Morgan et al. .......... 264/4.4 |
| 5,456,985 | A | 10/1995 | Zgoulli et al. .......... 428/402.2 |
| 5,573,934 | A | 11/1996 | Hubbell et al. |
| 5,670,209 | A | 9/1997 | Wyckoff |
| 5,766,637 | A | 6/1998 | Shine et al. |
| 5,780,056 | A | 7/1998 | Akamatsu et al. .......... 424/464 |
| 5,827,531 | A | 10/1998 | Morrison et al. |
| 5,993,851 | A | 11/1999 | Foldvari |
| 6,019,998 | A | 2/2000 | Nomoto et al. |
| 6,020,200 | A | 2/2000 | Enevold |
| 6,103,378 | A | 8/2000 | Yao et al. |
| 6,221,401 | B1 | 4/2001 | Zasadzinski et al. .......... 424/490 |
| 6,234,464 | B1 | 5/2001 | Krumbholz et al. |
| 6,274,174 | B1 | 8/2001 | Hom-ma et al. .......... 424/489 |
| 6,325,951 | B1 | 12/2001 | Soper et al. |
| 6,528,165 | B2 | 3/2003 | Chandler |
| 6,534,091 | B1 | 3/2003 | Garces Garces et al. ... 424/489 |
| 6,534,094 | B2 | 3/2003 | Moyano et al. |
| 6,534,926 | B1 | 3/2003 | Miller et al. |
| 6,544,926 | B1 | 4/2003 | Bodmer et al. |

FOREIGN PATENT DOCUMENTS

| EP | 0 301 777 | 2/1989 |
| EP | 0416575 | 3/1991 |

(Continued)

OTHER PUBLICATIONS

Abstract: Beestman; "Microencapsulation of Solid Particles," *Am. Chem. Soc.*, 2000, Accession No. 2000:793223.

(Continued)

*Primary Examiner*—Samuel A. Acquah
(74) *Attorney, Agent, or Firm*—Needle & Rosenberg, P.C.

(57) ABSTRACT

Described herein are microcapsules and emulsions prepared from low Bloom gelatin and methods of making and using thereof.

103 Claims, 3 Drawing Sheets

FOREIGN PATENT DOCUMENTS

| | | |
|---|---|---|
| EP | 1 116 516 | 7/2001 |
| GB | 2 115 768 | 9/1983 |
| JP | 1148338 | 6/1989 |
| WO | WO 92/11083 | 7/1992 |
| WO | WO 97/13416 | 4/1997 |
| WO | WO 2004/041251 A1 | 5/2004 |

OTHER PUBLICATIONS

Abstract: Kage et al., "Microencapsulation of mono-dispersed droplets by complex coacervation and menbrane thickness of generated capsules," Accession No.: 1997: 615273 CAPLUS.

Abstract: Yoshida et al., "Manufacture of microcapsules from complex coacervation processes," Accession No.: 1990:140735 CAPLUS.

Ijichi et al., "Multi-Layered Gelatin/Acacia Microcapsules by Complex Coacervation Method," *Journal of Chemical Engineering of Japan*, vol. 30(5), pp. 793-798, 1997.

Thimma et al., "Study of complex coacervation of gelatin with sodium carboxymethyl guar gum: Microencapsulation of clove oil and sulphamethoxazole," *J. Microencapsulation*, Vo;. 20(2), pp. 203-210, 2003.

U.S. Patent and Trademark Office—Office Action dated Feb. 10, 2005, Examiner: Samuel A. Acquah, U.S. Appl. No. 10/120,621, filed Apr. 11, 2002.

Response to Office Action dated Feb. 10, 1005, filed Mar. 2005.

U.S. Patent and Trademark Office—Office Action dated Nov. 20, 2003, Examiner: Samuel A. Acquah, U.S. Appl. No. 10/120,621, filed Apr. 11, 2002.

Response to Office Action dated Nov. 20, 2003, filed Apr. 13, 2004.

MICROCAPSULES AND EMULSIONS CONTAINING LOW BLOOM GELATIN AND METHODS OF MAKING AND USING THEREOF

BACKGROUND

The use of microcapsules for delivering compounds to a subject has been well-established. The selection of the microencapsulating material can vary depending upon the desired release pattern and the compound to be encapsulated. One such material that has been used is gelatin. Gelatins are widely used to formulate food products and drug formulations. A particular class of gelatins that are of interest are low Bloom gelatins. For example, fish gelatin has gained interest over the years as an alternative to bovine and porcine gelatin, especially as a result of concerns over BSE (1). Fish gelatin can also be a kosher product unlike porcine gelatin. Fish gelatin produced from warm water fish has Bloom numbers similar to bovine and porcine gelatin with less undesirable off-flavor and off-odor (2), but it is a limited resource and commands a higher price. In contrast, gelatin from cold water fish has no Bloom number but comes from less utilised resources. Thus, there is a strong economic justification for the attempt to use a low Bloom fish gelatin over high Bloom gelatin. Additionally, the use of low Bloom gelatin requires lower reaction temperatures, which can prolong the stability of the microencapsulated compound as well as reduce processing times and reduce energy consumption. Described herein are microcapsules and emulsions prepared from low Bloom gelatin and methods of making and using thereof.

SUMMARY

Described herein are microcapsules and emulsions prepared from low Bloom gelatin and methods of making and using thereof. The advantages described herein will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
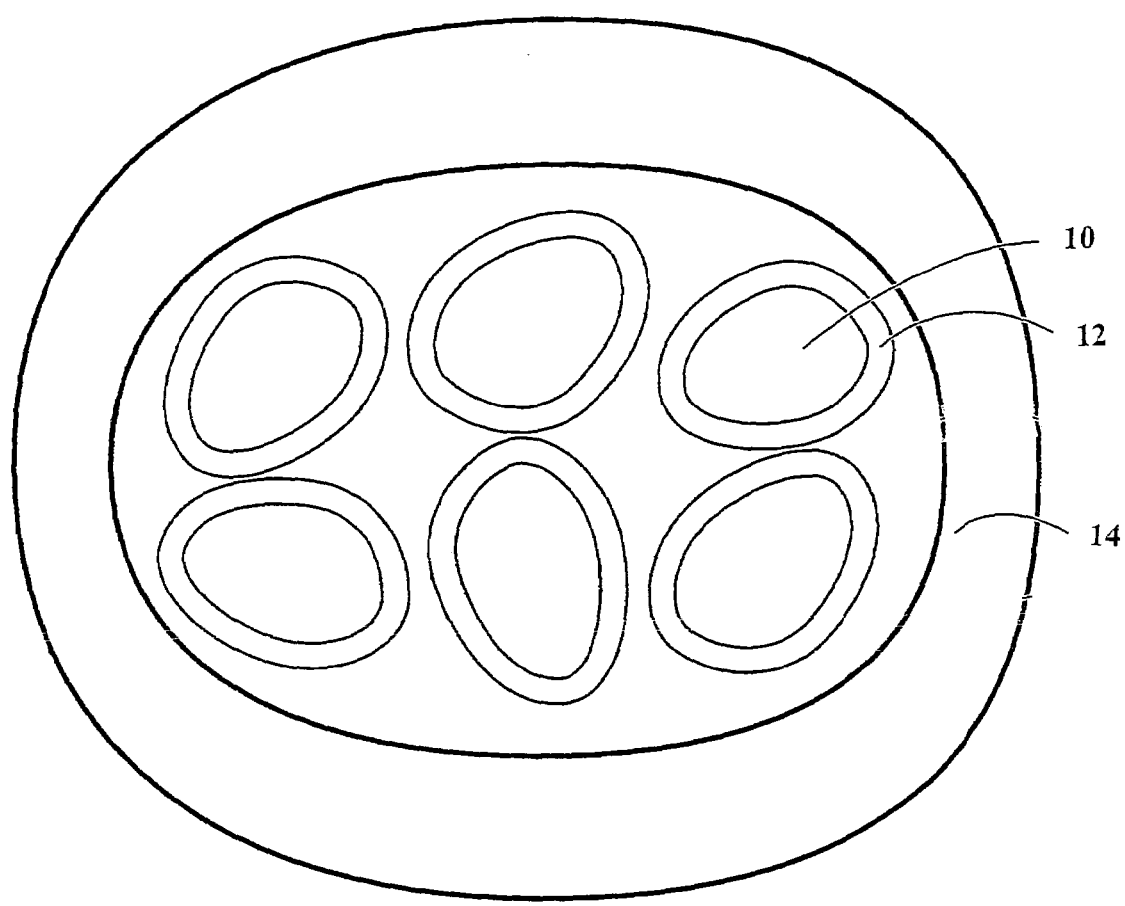
FIG. 1 shows a drawing of a multicore microcapsule.

Before the present compounds, composites, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

I. Compositions

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A–D is disclosed, then even if each is not individually recited, each is individually and collectively contemplated. Thus, in this example, each of the combinations A–E, A–F, B–D, B–E, B–F, C–D, C–E, and C–F are specifically contemplated and should be considered disclosed from disclosure of A, B, and C; D, E, and F; and the example combination A–D. Likewise, any subset or combination of these is also specifically contemplated and disclosed. Thus, for example, the sub-group of A–E, B–F, and C–E are specifically contemplated and should be considered disclosed from disclosure of A, B, and C; D, E, and F; and the example combination A–D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

a. Microcapsules

In one aspect, described herein are microcapsules comprising an agglomeration of primary microcapsules and a loading substance, each individual primary microcapsule having a primary shell, wherein the loading substance is encapsulated by the primary shell, wherein the agglomeration is encapsulated by an outer shell, wherein the primary shell and/or the outer shell comprises gelatin having a Bloom number less than 50. These microcapsules are referred to herein as "multicore microcapsules." Referring to FIG. 1, the loading substance is in core 10 and surrounded by primary shell 12. The primary shells are then encapsulated by outer shell 14.

Figure 2:
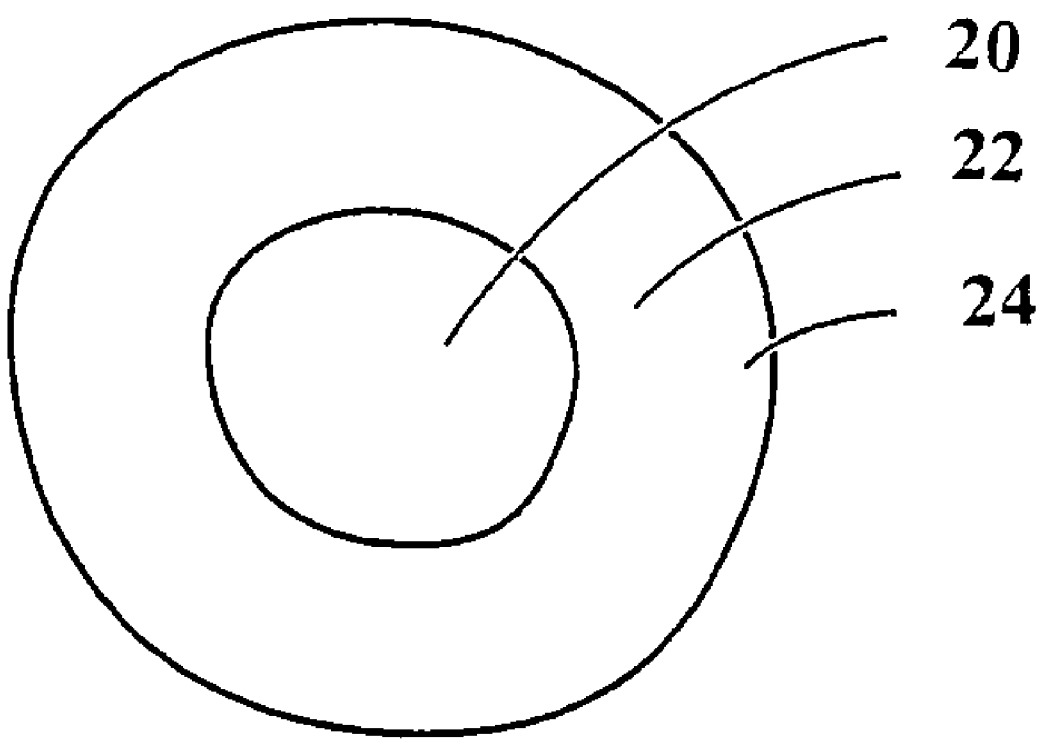
FIG. 2 shows a drawing of a single-core microcapsule.
Figure 3:
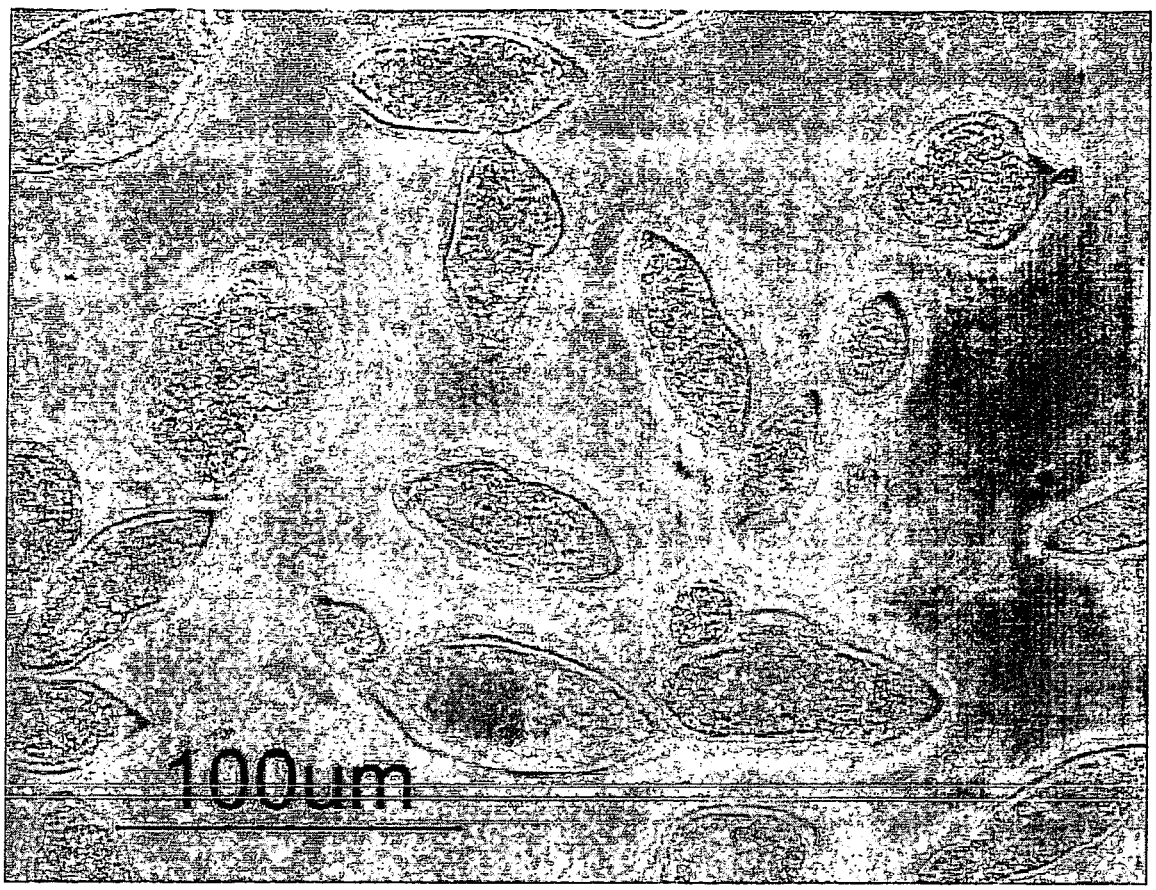
FIG. 3 shows microcapsules (60% loading substance) prepared by emulsification of fish oil in a zero Bloom fish gelatin solution (40° C.) at 7,500 rpm for 5 minutes, followed by complex coacervation, cooling to 4° C. and crosslinking with a transglutaminase.

In another aspect, described herein are microcapsules comprising a loading substance, a primary shell, and a secondary shell, wherein the primary shell encapsulates the loading substance, and the secondary shell encapsulates the loading substance and primary shell, wherein the primary shell and/or the secondary shell comprises gelatin having a Bloom number less than 50. These microcapsules are referred to herein as "single-core microcapsules." Referring to FIG. 2, the loading substance is in core 20 and surrounded by primary shell 22. The primary shell is then encapsulated by the secondary shell 24.

The loading substance can be any substance that is not entirely soluble in the aqueous mixture. In one aspect, the loading substance is a solid, a hydrophobic liquid, or a mixture of a solid and a hydrophobic liquid. In another aspect, the loading substance comprises a grease, an oil, a lipid, a drug (e.g., small molecule), a biologically active substance, a nutritional supplement (e.g., vitamins), a flavour compound, or a mixture thereof. Examples of oils include, but are not limited to, animal oils (e.g., fish oil, marine mammal oil, etc.), vegetable oils (e.g., canola or rapeseed), mineral oils, derivatives thereof or mixtures thereof. The loading substance can be a purified or partially purified oily substance such as a fatty acid, a triglyceride or ester thereof, or a mixture thereof. In another aspect, the loading substance can be a carotenoid (e.g., lycopene), a satiety agent, a flavor compound, a drug (e.g., a water insoluble drug), a particulate, an agricultural chemical (e.g., herbicides, insecticides, fertilizers), or an aquaculture ingredient (e.g., feed, pigment). When the loading the loading substance is a fish oil, any fish oil can be used. Specific examples of suitable fish oils include, but are not limited to, Atlantic fish oils, Pacific fish oils, Mediterranean fish oils, light pressed fish oil, alkaline treated fish oil, heat treated fish oil, light and heavy brown fish oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonids oil, shark oil, and the like.

In one aspect, the loading substance comprises one or more fatty acids. In one aspect, the fatty acid comprises at least 10, at least 12, at least 14, at least 16, at least 18, or at least 20 carbon atoms. In some specific examples, the fatty acids and residues thereof can contain 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. In other examples, the fatty acids can comprise a mixture of fatty acids having a range of carbon atoms. For example, the fatty acids can comprise from about 6 to about 40, from about 12 to about 38, from about 14 to about 36, from about 16 to about 34, from about 18 to about 32, or from about 20 to 30 carbon atoms.

The fatty acids can be saturated, unsaturated, or a mixture of saturated and unsaturated fatty acids. By "saturated" is meant that the molecule contains no carbon—carbon double or triple bounds. By "unsaturated" is meant that the molecule contains at least one carbon—carbon double or triple bond.

In one aspect, the loading substance can be an omega-3 fatty acid. Examples of omega-3 fatty acids include, but are not limited to, α-linolenic acid (18:3ω3), octadecatetraenoic acid (18:4ω3), eicosapentaenoic acid (20:5ω3) (EPA), docosahexaenoic acid (22:6ω3) (DHA), docosapentaenoic acid (22:5ω3) (DPA), eicosatetraenoic acid (20:4ω3), uncosapentaenoic acid (21:5ω3), docosapentaenoic acid (22:5ω3) and derivatives thereof and mixtures thereof. Many types of derivatives of omega-3 fatty acids are well known in the art. Examples of suitable derivatives include, but are not limited to, esters, such as phytosterol esters, branched or unbranched $C_1$–$C_{30}$ alkyl esters, branched or unbranched $C_2$–$C_{30}$ alkenyl esters, or branched or unbranched $C_3$–$C_{30}$ cycloalkyl esters such as phytosterol esters and $C_1$–$C_6$ alkyl esters. Sources of oils can be derived from aquatic organisms (e.g., anchovies, capelin, Atlantic cod, Atlantic herring, Atlantic mackerel, Atlantic menhaden, salmonids, sardines, shark, tuna, etc) and plants (e.g., flax, vegetables, etc) and microorganisms (e.g., fungi and algae).

In one aspect, the loading substance can contain an antioxidant. Examples of antioxidants include, but are not limited to, vitamin E, $CoQ_{10}$, tocopherols, lipid soluble derivatives of more polar antioxidants such as ascobyl fatty acid esters (e.g., ascobyl palmitate), plant extracts (e.g., rosemary, sage and oregano oils), algal extracts, and synthetic antioxidants (e.g., BHT, TBHQ, ethoxyquin, alkyl gallates, hydroquinones, tocotrienols).

One or more of the shell layers in the single and multicore microcapsules comprises gelatin having a Bloom number less than 50. This gelatin is referred to herein as "low Bloom gelatin." The Bloom number describes the gel strength formed at 10° C. with a 6.67% solution gelled for 18 hours. In one aspect, the low Bloom gelatin has a Bloom number less than 40, less than 30, less than 20, or less than 10. In another aspect, the gelatin has a Bloom number of 45, 40, 35, 30, 25, 20, 15, 10, 9, 8, 7, 6, 5, 4, 3, 2, 1, or 0, where any two values can be used to produce a range. In another aspect, the low Bloom gelatin is in both the primary shell and the outer shell of the multicore microcapsule. In one aspect, the low Bloom gelatin is gelatin type A. In another aspect, the low Bloom gelatin is gelatin type A produced by Kenney & Ross Ltd., R.R. #3 Shelburne, NS Canada.

Other polymers may be present in the shell layers of the single and multicore microcapsules besides low Bloom gelatin. Examples of such polymers include, but are not limited to, a protein, a polyphosphate, a polysaccharide, or a mixture thereof. In another aspect, the shell material used to prepare the single- and multicore microcapsules further comprises high Bloom gelatin type A (Bloom number greater than or equal to 50), gelatin type B, polyphosphate, gum arabic, alginate, chitosan, carrageenan, pectin, starch, modified starch, alfa-lactalbumin, beta-lactoglobumin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, or a mixture thereof. It is also contemplated that derivatives of these polymers can be used as well. In another aspect, the polymer can be kosher gelatin, non-kosher gelatin Halal gelatin, or non-Halal gelatin.

In one aspect, the material used to make the shells of the single- or multicore microcapsules is a two-component system made from a mixture of low Bloom gelatin and one or more different types of polymers. In one aspect, the material is a complex coacervate between low Bloom gelatin and one or more polymer components. Complex coacervation is caused by the interaction between two oppositely charged polymers. In one aspect, the shell material used to produce the single and multicore microcapsules is composed of (1) low Bloom gelatin and (2) gelatin type B, polyphosphate, gum arabic, alginate, chitosan, carrageenan, pectin, starch, modified starch, alfa-lactalbumin, beta-lactoglobumin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, or a mixture thereof. The dry weight ratio of low Bloom gelatin to the other polymer component depends on the loading substance and polymer selected. In one aspect, the molar ratio is from 1:5 to 15:1. For example, when low Bloom gelatin and polyphosphate are used, the dry weight ratio of low Bloom gelatin to polyphosphate is about 8:1 to about 12:1; when low Bloom gelatin and gelatin type B are used, the dry weight ratio is 2:1 to 1:2; and when low Bloom gelatin and alginate are used, the dry weight ratio is 3:1 to 20:1. The amount of low Bloom gelatin and other polymer components provided in the aqueous mixture is typically sufficient to form both the primary shells and the outer shells of the encapsulated agglomeration of microcapsules. In one aspect, the low Bloom gelatin is provided in an amount of from about 1% to about 15% by weight of the aqueous mixture, from about 3% to about 8% by weight, or from about 6% by weight.

Processing aids can be included in the shell material (e.g., primary or outer shells). Processing aids can be used for a variety of reasons. For example, they may be used to promote agglomeration of the primary microcapsules, stabilize the emulsion system, improve the properties of the outer shells, control microcapsule size and/or to act as an antioxidant. In one aspect, the processing aid can be an emulsifier, a fatty acid, a lipid, a wax, a microbial cell (e.g., yeast cell lines), a clay, or an inorganic compound (e.g., calcium carbonate). Not wishing to be bound by theory, these processing aids can improve the barrier properties of the microcapsules. In one aspect, one or more antioxidants can be added to the shell material. Antioxidant properties are useful both during the process (e.g. during coacervation and/or spray drying) and in the microcapsules after they are formed (i.e. to extend shelf-life, etc). Preferably a small number of processing aids that perform a large number of functions can be used. In one aspect, the antioxidant can be a phenolic compound, a plant extract, or a sulphur-containing amino acid. In one aspect, ascorbic acid (or a salt thereof such as sodium or potassium ascorbate) can be used to promote agglomeration of the primary microcapsules, to control microcapsule size and to act as an antioxidant. The antioxidant can be used in an amount of about 100 ppm to about 12,000 ppm, or from about 1,000 ppm to about 5,000 ppm. Other processing aids such as, for example, metal chelators, can be used as well. For example, ethylene diamine tetraacetic acid can be used to bind metal ions, which can reduce the catalytic oxidation of the loading substance.

In one aspect, the primary microcapsules (primary shells) have an average diameter of about 40 nm to about 10 $\mu$m, 0.1 $\mu$m to about 10 $\mu$m, 1 $\mu$m to about 10 $\mu$m, 1 $\mu$m to about 8 $\mu$m, 1 $\mu$m to about 6 $\mu$m, 1 $\mu$m to about 4 $\mu$m, or 1 $\mu$m to about 2 $\mu$m, or 1 $\mu$m. In another aspect, the multicore microcapsules can have an average diameter of from about 1 $\mu$m to about 2000 $\mu$m, 20 $\mu$m to about 1000 $\mu$m, from about 20 $\mu$m to about 100 $\mu$m, or from about 30 $\mu$m to about 80 $\mu$m.

In another aspect, the single-core microcapsules have an outer diameter of from 1 $\mu$m to 2,000 $\mu$m.

The microcapsules described herein generally have a combination of high payload and structural strength. For example, payloads of loading substance can be from 20% to 90%, 50% to 70% by weight, or 60% by weight of the single or multicore microcapsules.

It is also contemplated that one or more additional shell layers can be placed on the outer shell of the single or multicore microcapsules. The techniques described in International Publication No. WO 2004/041251 A1, which is incorporated by reference in its entirety, can be used to add additional shell layers to the single and multicore microcapsules.

The microcapsules described herein have good rupture strength to help reduce or prevent breaking of the microcapsules during use (e.g., incorporation into food or other formulations). Indeed, the microcapsules described herein are stable even in boiling water. Furthermore, the microcapsule's shells are for the most part insoluble in both aqueous and oily media, and can help reduce or prevent oxidation and/or deterioration of the loading substance during preparation of the microcapsules, during long-term storage, and/or during incorporation of the microcapsules into a formulation vehicle, and/or during storage of a formulation vehicle containing the microcapsules.

b. Emulsions

In another aspect, any of the low Bloom gelatins can be used to stabilize emulsions containing any of the loading substances described herein. For example, the low Bloom gelatin can be admixed with an aqueous solution (i.e., emulsion) of loading substance such as, for example, fish oil, which contains optional additives such as antioxidants, emulsifiers (surfactants), metal ion chelators, flavorants, or viscosifiers (polysaccharides). In this example, the emulsion can then be "washed" with nitrogen gas to remove any off-odors and packaged under nitrogen. In one aspect, the emulsion further comprises a protein, a polyphosphate, a polysaccharide, or a mixture thereof. In another aspect, the emulsion further comprises gelatin type A, gelatin type B, polyphosphate, gum arabic, alginate, chitosan, carrageenan, pectin, starch, modified starch, alfa-lactalbumin, beta-lactoglobumin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, or a mixture thereof. In a further aspect, the gelatin has a Bloom number of zero. The resultant emulsions can then be incorporated into a foodstuff or other formulation.

There are several advantages to using low Bloom gelatin as a stabilizer of emulsions. First, the no Bloom gelatin has a gelation temperature close to refrigeration temperature, and remains as a liquid when it is above refrigeration temperature. Thus the emulsion will not form a gel at room temperature. Second, the emulsion can be produced at or below room temperature, which allows the loading materials such as, for example, fish oil, to avoid harsh conditions (e.g., high process temperatures), which can be detrimental to the stability of the loading substance.

In one aspect, the emulsion has a loading payload of 20 to 90%, 50 to 70%, or 60% based on dry weight. In one aspect, the emulsion can be in the form of an aqueous mixture, which can then be used as is. In another aspect, the emulsion can be dried to form a microcapsule using the techniques described below. The microcapsule can exist in a variety of different forms depending upon the drying technique used. For example, the microcapsule (e.g., single or multicore) can be in a polymeric matrix. In one aspect, the loading substance has a primary shell and is exposed to a matrix of one or more different polymers. The dried emulsion may contain no water or small amounts of moisture (from 5% or less by weight of the emulsion).

II. Methods for Making Microcapsules

Described herein are methods for preparing microcapsules. In one aspect, the method comprises:

(a) providing an aqueous mixture comprising a loading substance, a gelatin having a Bloom number less than 50 (referred to herein as "a first polymer component"), (b) adjusting the pH, temperature, concentration, mixing speed or a combination thereof to form a primary shell comprising the gelatin around the loading substance;

(c) further adjusting pH and cooling the aqueous mixture to a temperature above the gel point of the gelatin until the primary shells form an agglomeration; and, (d) cooling the aqueous mixture to form an outer shell around the agglomeration.

In step (a), the loading substance and the low Bloom gelatin can be admixed in any order. It is also contemplated that any of the polymers described above (referred to herein as the "second polymer component") can be admixed in step (a). The aqueous mixture may be a mechanical mixture, a suspension or an emulsion. When a liquid loading material is used, particularly a hydrophobic liquid, the aqueous mixture is preferably an emulsion of the loading material, the low Bloom gelatin, and the optional second polymer component. Any of the loading substances and polymers described above can be used in the methods described herein to produce the microcapsules.

In one aspect, step (a) comprises (i) dispersing the loading substance into the aqueous mixture of the low Bloom gelatin and (ii) adding the second polymer to the aqueous mixture of loading substance and gelatin. In one aspect, a processing aid such as, for example, an antioxidant, can be added as well. In this aspect, the loading substance can then be dispersed into the aqueous mixture, for example, by using a homogenizer. Not wishing to be bound by theory, if the loading substance is a hydrophobic liquid, an emulsion can be formed, in which a fraction of the low Bloom gelatin (or its complex with the second polymer component) begins to deposit around individual droplets of loading substance to form the primary shells. If the loading substance is a solid particle, a suspension is formed in which a fraction of the low Bloom gelatin (or its complex with the second polymer component) begins to deposit around individual particles to begin the formation of primary shells. At this point, another aqueous solution of first and/or second polymer component can be added to the aqueous mixture if it is not added before the emulsification step.

In one aspect, after the loading substance, the low Bloom gelatin, and the optional second polymer component have been admixed, the admixture can be emulsified. Not wishing to be bound by theory, by varying the emulsification speed it is possible to produce single or multicore microcapsules. For example, when lower emulsification speeds are used (e.g., 1,000 to 2,000 rpm) are used, the droplets of the loading substance are large enough to form a single particle, which upon encapsulation, produces a single core microcapsule. Conversely, if high emulsification speeds (e.g., 5,000 to 15,000 rpm), the resultant droplets of loading substance are small (e.g., from 1 to 10 $\mu$m). These tiny droplets have higher surface energy and will readily form agglomerations when pH and/or temperature is adjusted accordingly, which results in the formation of multicore microcapsules upon encapsulation. The emulsification step can be achieved by techniques known in the art including, but not limited to, homogenization and high pressure/high shear pumps.

In one aspect, droplets or particles of the loading substance in the aqueous mixture have an average diameter of less than 100 $\mu$m, less than 75 $\mu$m, less than 50 $\mu$m, and less than 25 $\mu$m. Droplets or particles of the loading substance having an average diameter less than 10 $\mu$m, less than 5 $\mu$m, less than 3 $\mu$m or less than 1 $\mu$m can be used. Particle size can be measured using any typical equipment known in the art, for example, a Coulter™ LS230 Particle Size Analyzer, Miami, Fla., USA.

The pH, temperature, concentration, mixing speed or a combination thereof is then adjusted to accelerate the formation of the primary shells around the droplets or particles of the loading substance. In one aspect, the low Bloom gelatin and the second polymer component will form a complex coacervation, which further deposits around the loading substance to form primary shells of shell material. The pH adjustment depends on the type of shell material to be formed. In one aspect, the pH may be adjusted to a value from 3.5 to 5.0, or from 4.0 to 5.0. If the pH of the mixture starts in the desired range, then little or no pH adjustment is required. In one aspect, the initial temperature of the aqueous mixture is from about 20° C. to about 60° C., or about 30 to 50° C. Mixing can be adjusted so that there is good mixing without breaking the microcapsules as they form. Particular mixing parameters depend on the type of equipment being used. Any of a variety of types of mixing equipment known in the art may be used. In one aspect, an axial flow impeller, such as Lightnin™ A310 or A510, can be used.

The aqueous mixture can then be cooled under controlled cooling rate and mixing parameters to permit agglomeration of the primary shells to form encapsulated agglomerations of primary shells. Not wishing to be bound by theory, the encapsulated agglomerations are discrete particles themselves. It is advantageous to control the formation of the encapsulated agglomerations at a temperature above the gel point of the shell material, and to let excess shell material form a thicker outer shell. It is also possible at this stage to add more polymer, where the polymer is the same or different, in order to thicken the outer shell and/or produce microcapsules having primary and outer shells of different composition. In one aspect, the temperature is lowered at a rate of 1° C./10 minutes until it reaches a temperature of from about 0° C. to about 10° C., or about 5° C. The outer shell encapsulates the agglomeration of primary shells to form a rigid encapsulated agglomeration of microcapsules.

A cross-linker may be added to further increase the rigidity of the single and multicore microcapsules by cross-linking the shell material in both the outer and primary shells and to make the shells insoluble in both aqueous and oily media. In one aspect, the cross-linker is added after the outer shell of the microcapsule is produced. Any suitable cross-linker can be used and the choice of cross-linker can vary depending upon the selection of the low Bloom gelatin and second polymer component. In one aspect, the cross-linkers can be enzymatic cross-linkers (e.g. transglutaminase), aldehydes (e.g. formaldehyde or gluteraldehyde), tannic acid, alum or a mixture thereof. In another aspect, the cross-linker can be a plant extract or a phenolic. It is also contemplated that one or more loading substances (e.g., antioxidants) can be used with the cross-linker. When the microcapsules are to be used to deliver a biologically active substance to an organism, the cross-linkers are preferably non-toxic or of sufficiently low toxicity. The amount of cross-linker used depends on the low Bloom gelatin and other components selected and can be adjusted to provide more or less structural rigidity as desired. In one aspect, the amount of cross-linker that can be used is in the amount of about 0.1%, to about 5.0%, 0.5% to about 5.0%, 1.0% to about 5.0%, about 2.0% to about 4.0%, or about 2.5%, by weight of the low Bloom gelatin. In general, one skilled in the art may routinely determine the desired amount in any given case by simple experimentation.

In one aspect, the microcapsules can be washed with water and/or dried to provide a free-flowing powder. Drying can be accomplished by a number of methods known in the art such as, for example, freeze drying, drying with ethanol, or spray drying. In one aspect, spray drying can be used for drying the microcapsules. Spray drying techniques are disclosed in "Spray Drying Handbook", K. Masters, 5$^{th}$ edition, Longman Scientific Technical UK, 1991, the disclosure of which is hereby incorporated by reference.

In another aspect, described herein is a process for preparing microcapsules, the process comprising:
(a) providing an emulsion comprising a loading substance and a gelatin having a Bloom number less than 50; and
(b) drying the emulsion to produce the microcapsules.

Any of the loading substances and low Bloom gelatins described herein can be used in this embodiment. Furthermore, by adjusting the pH, temperature, concentration, mixing speed or a combination thereof, it is possible to prepare single or multicore microcapsules prior to drying. In general, the emulsion prior to drying step (a) is an aqueous emulsion. It is also contemplated that any of the second polymer components described above can be used in combination with the low Bloom gelatin to produce the powder. The drying step can be any technique known in the art including, but not limited to, spray drying, fluidized bed drying, freeze drying, or drum drying. When the drying technique is spray drying, the drying step requires short process times, which can reduce possible degradation of the loading substance.

III. Use of Microcapsules

The microcapsules described herein can be used to prepare liquids as free-flowing powders or compressed solids, to store a substance, to separate reactive substances, to reduce toxicity of a substance, to protect a substance against oxidation, to deliver a substance to a specified environment and/or to control the rate of release of a substance. In one aspect, the microcapsules and emulsions described herein can be used for delivering any of the loading substances described herein to a subject. Examples of subjects include mammals such as mice, rats, cows or cattle, horses, sheep, goats, and primates, including apes, chimpanzees, orangatangs, fish, shellfish, crustaceans, birds (e.g., chickens, roosters, etc.), humans or domesticated animals (e.g., dogs and cats).

Also disclosed herein are foodstuffs comprising any of the microcapsules and emulsions disclosed herein. By "foodstuff" is meant any article that can be consumed (e.g., eaten, drank, or ingested) by a subject. In one aspect, the microcapsules can be used as nutritional supplements to a foodstuff. For example, the microcapsules and emulsions can be loaded with vitamins, omega-3 fatty acids, and other compounds that provide health benefits. In one aspect, the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or pet companion food. In another aspect, the foodstuff is bread, tortillas, cereal, sausage, chicken, ice cream, yogurt, milk, salad dressing, rice bran, fruit juice, a dry beverage powder, rolls, cookies, crackers, fruit pies, or cakes.

In one aspect, provided are pharmaceutical formulations comprising any of the microcapsules or emulsions described herein and a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy* (19th ed.) Gennaro, ed., Mack Publishing Company, Easton, Pa., 1995, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, antiinflammatory agents, anesthetics, and the like.

The pharmaceutical formulation can be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic esters such as ethyl oleate.

Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids or binders may be desirable.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The microcapsules and emulsions can be used to treat or prevent a variety of diseases depending upon the selection of the loading substance. For example, when the loading substance is an omega-3 fatty acid, the microcapsule can be used to lower cholesterol levels, triglyceride levels, or a combination thereof in a subject.

EXAMPLE

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Zero Bloom high molecular weight fish gelatin provided by Kenney & Ross Ltd., R.R. #3 Shelburne, NS Canada (44.0 g) was mixed with 482.0 g of distilled water. The gelatin dissolved after being dispersed in water and heated at 25° C., where a reactor was connected to a circulator with the temperature set at 25° C. Distilled water (889.0 g) was added to the reactor and the temperature was controlled by the circulator (25° C.).

After the gelatin dissolved, the mixture was heated up to 35.2° C. Fish oil (72.0 g) was mixed with the gelatin and emulsified at 7500 rpm for 5 minutes. An emulsion formed and contained oil droplets about 1–5 $\mu$m in diameter. The emulsion was added to the reactor, which contained water at 25° C. The mixture had a pH value of 6. Sodium ascorbate (7.3 g) was added to the mixture. An aliquot of 88.1 g of 5% w/w sodium polyphosphate solution at room temperature was further added to the reactor. The pH value was adjusted to 4.7, which permitted the agglomeration to grow up to about 50 $\mu$m as determined by an optical microscope.

The above suspension containing the microcapsule agglomerations was then cooled to 4° C. within 2.5 hr. An enzyme preparation of transglutaminase was added at 1% w/w and the temperature was adjusted to 5° C. for crosslinking for 5 hr followed by 20° C. for emzymatic hardening for 9 hr. The finished suspension of microcapsules was spray dried. The microcapsules were a free flowing powder and the surface free oil was below 0.1% w/w.

Throughout this application, various publications are referenced. The disclosures of these publications in their entireties are hereby incorporated by reference into this application in order to more fully describe the compounds, compositions and methods described herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

REFERENCES

1. Haug, I. J., Draget, K. I. and Smidsrod, O., Physical and Rheological Properties of Fish Gelatin Compared to Mammalian Gelatin, Food Hydrocolloids, 18 (2004) 203–213.
2. Choi, S. S. and Regenstein, J. M., Physicochemical and Sensory Characteristics of Fish Gelatin, J. of Food Science: Food Chemistry and Toxicology, 65 (2000) 194–199.

What is claimed is:

1. A microcapsule comprising an agglomeration of primary microcapsules and a loading substance, each individual primary microcapsule having a primary shell, wherein the loading substance is encapsulated by the primary shell, wherein the agglomeration is encapsulated by an outer shell, wherein the primary shell and/or the outer shell comprises gelatin having a Bloom number less than 50.

2. The microcapsule of claim 1, wherein the primary shell and/or the outer shell further comprises a protein, a polyphosphate, a polysaccharide, or a mixture thereof.

3. The microcapsule of claim 1, wherein the primary shell and/or the outer shell further comprises high Bloom gelatin type A, gelatin type B, polyphosphate, gum arabic, alginate, chitosan, carrageenan, pectin, starch, modified starch, alfa-lactalbumin, beta-lactoglobulin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, kosher gelatin, non-kosher gelatin, Halal gelatin, non-Halal gelatin, or a mixture thereof.

4. The microcapsule of claim 1, wherein the primary shell and the outer shell comprises a complex coacervate.

5. The microcapsule of claim 1, wherein the gelatin has a Bloom number of less than 40.

6. The microcapsule of claim 1, wherein the gelatin has a Bloom number of less than 30.

7. The microcapsule of claim 1, wherein the gelatin has a Bloom number of less than 20.

8. The microcapsule of claim 1, wherein the gelatin has a Bloom number of less than 10.

9. The microcapsule of claim 1, wherein the gelatin has a Bloom number of zero.

10. The microcapsule of claim 1, wherein the gelatin is gelatin type A having a Bloom number of zero.

11. The microcapsule of claim 1, wherein the primary shell and the outer shell comprises gelatin having a Bloom number of less than 50.

12. The microcapsule of claim 1, wherein the primary shell and the outer shell comprises a complex coacervate between gelatin having a Bloom number of zero and polyphosphate.

13. The microcapsule of claim 1, wherein the microcapsule further comprises an antioxidant.

14. The microcapsule of claim 13, wherein the antioxidant comprises a phenolic compound, a plant extract, or a sulphur-containing amino acid.

15. The microcapsule of claim 13, wherein the antioxidant comprises ascorbic acid or a salt of ascorbic acid.

16. The microcapsule of claim 1, wherein the outer shell has an average diameter of from about 1 μm to about 2,000 μm.

17. The microcapsule of claim 1, wherein the outer shell has an average diameter of from about 20 μm to about 1,000 μm.

18. The microcapsule of claim 1, wherein the outer shell has an average diameter of from about 20 μm to about 100 μm.

19. The microcapsule of claim 1, wherein the outer shell has an average diameter of from about 30 μm to about 80 μm.

20. The microcapsule of claim 1, wherein the primary shells have an average diameter of from about 40 μm to about 10 μm.

21. The microcapsule of claim 1, wherein the primary shells have an average diameter of from about 0.1 μm to about 5 μm.

22. The microcapsule of claim 1, wherein the primary shells have an average diameter of about 1 μm.

23. The microcapsule of claim 1, wherein the loading substance is from 20% to 90% by weight of the microcapsule.

24. The microcapsule of claim 1, wherein the loading substance is from 50% to 70% by weight of the microcapsule.

25. The microcapsule of claim 1, wherein the loading substance comprises a grease, an oil, a lipid, a drug, a biologically active substance, a nutritional supplement, a flavour compound, or a mixture thereof.

26. The microcapsule of claim 1, wherein the loading substance comprises fish oil.

27. The microcapsule of claim 1, wherein the loading substance comprises an omega-3 fatty acid or an ester or triglyceride of an omega-3 fatty acid.

28. The microcapsule of claim 1, wherein the loading substance comprises eicosapentaenoic acid, docosahexaenoic acid, docosapentaenoic acid, an ester or triglyceride thereof, or a mixture thereof.

29. The microcapsule of claim 1, wherein the loading substance comprises a phytosterol ester of docosahexaenoic acid and/or eicosapentaenoic acid, a $C_1$–$C_6$ alkyl ester of docosahexaenoic acid and/or eicosapentaenoic acid, an ester or triglyceride thereof, or a mixture thereof.

30. The microcapsule of claim 1, wherein the primary shell and the outer shell comprises a complex coacervate between gelatin having a Bloom number of zero and polyphosphate, and the loading substance comprises eicosapentaenoic acid, docosahexaenoic acid, docosapentaenoic acid, an ester or triglyceride thereof, or a mixture thereof.

31. The microcapsule of claim 1, wherein the loading substance further comprises an antioxidant, wherein the antioxidant comprises $CoQ_{10}$, vitamin E, a tocopherol, a lipid soluble derivative of a polar antioxidant, a plant extract, an algal extract, or a synthetic antioxidant.

32. The microcapsule of claim 1, further comprising one or more additional shells surrounding the outer shell, wherein at least one of the primary, outer, and additional shells comprise a complex coacervate.

33. The microcapsule of claim 1, further comprising one or more processing aid in the primary and/or the outer shells, wherein the processing aid comprises an emulsifier, a fatty acid, a lipid, a wax, a microbial cell, a clay, an inorganic compound, or any combination thereof.

34. A microcapsule comprising a loading substance, a primary shell, and a secondary shell, wherein the primary shell encapsulates the loading substance, and the secondary shell encapsulates the loading substance and primary shell, wherein the primary shell and/or the secondary shell comprises gelatin having a Bloom number less than 50.

35. The microcapsule of claim 34, wherein the primary shell and the secondary shell comprises a complex coacervate.

36. The microcapsule of claim 34, wherein the primary shell and/or the secondary shell further comprises a protein, a polyphosphate, a polysaccharide, or a mixture thereof.

37. The microcapsule of claim 34, wherein the primary shell and/or the secondary shell further comprises high Bloom gelatin type A, gelatin type B, polyphosphate, gum arabic, alginate, chitosan, carrageenan, pectin, starch, modified starch, alfa-lactalbumin, beta-lactoglobulin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, kosher gelatin, non-kosher gelatin, Halal gelatin, non-Halal gelatin, or a mixture thereof.

38. The microcapsule of claim 34, wherein the gelatin is gelatin type A having a Bloom number of zero.

39. The microcapsule of claim 34, wherein the primary and/or secondary shell comprises a complex coacervate between zero Bloom gelatin and polyphosphate.

40. The microcapsule of claim 34, wherein the loading substance is from 20% to 90% by weight of the microcapsule.

41. The microcapsule of claim 34, wherein the loading substance is from 50% to 70% by weight of the microcapsule.

42. The microcapsule of claim 34, wherein the microcapsule has a diameter of from 1 μm to 2,000 μm.

43. The microcapsule of claim 34, wherein the microcapsule has a diameter of from 20 μm to 100 μm.

44. The microcapsule of claim 34, wherein the microcapsule has a diameter of from 30 μm to 80 μm.

45. An emulsion comprising a loading substance and a gelatin having a Bloom number less than 50.

46. The emulsion of claim 45, wherein the emulsion further comprises a protein, a polyphosphate, a polysaccharide, or a mixture thereof.

47. The emulsion of claim 45, wherein the emulsion further comprises high Bloom gelatin type A, gelatin type B, polyphosphate, gum arabic, alginate, chitosan, carrageenan, pectin, starch, modified starch, alfa-lactalbumin, beta-lactoglobumin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, kosher gelatin, Halal gelatin, or a mixture thereof.

48. The emulsion of claim 45, wherein the emulsion further comprises an antioxidant, a surfactant, a metal ion chelator, a flavorant, or a viscosifier.

49. The emulsion of claim 45, wherein the gelatin is gelatin type A having a Bloom number of zero.

50. A process for preparing microcapsules, the process comprising:
    (a) providing an aqueous mixture comprising a loading substance and a gelatin having a Bloom number less than 50;
    (b) adjusting the pH, temperature, concentration, mixing speed or a combination thereof to form a primary shell comprising the gelatin around the loading substance;
    (c) cooling the aqueous mixture to a temperature above the gel point of the gelatin until the primary shells form an agglomeration; and,
    (d) cooling the aqueous mixture to form an outer shell around the agglomeration.

51. The process of claim 50, wherein the aqueous mixture further comprises a second polymer component.

52. The process of claim 51, wherein the second polymer component comprises a protein, a polyphosphate, a polysaccharide, or a mixture thereof.

53. The process of claim 51, wherein the second polymer component comprises high Bloom gelatin type A, gelatin type B, polyphosphate, gum arabic, alginate, chitosan, carrageenan, pectin, starch, modified starch, alfa-lactalbumin, beta-lactoglobumin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, kosher gelatin, non-kosher gelatin, Halal gelatin, non-Halal gelatin, or a mixture thereof.

54. The process of claim 51, wherein the second polymer component is polyphosphate.

55. The process of claim 50, wherein the loading substance comprises a grease, an oil, a lipid, a drug, a biologically active substance, a nutritional supplement, a flavour compound, or a mixture thereof.

56. The process of claim 50, wherein the loading substance comprises fish oil.

57. The process of claim 50, wherein the loading substance comprises an omega-3 fatty acid or an ester or triglyceride of an omega-3 fatty acid.

58. The process of claim 50, wherein the loading substance comprises eicosapentaenoic acid, docosahexaenoic acid, docosapentaenoic acid, an ester or triglyceride, or a mixture thereof.

59. The process of claim 50, wherein the loading substance is provided in an amount of from about 20% to 90% by dry weight.

60. The process of claim 50, wherein the low Bloom gelatin is provided in an amount of from about 1% to about 15% by weight of the aqueous mixture.

61. The process of claim 50, wherein an antioxidant is added to the aqueous mixture in step (a).

62. The process of claim 50, wherein step (a) comprises (i) dispersing the loading substance into the aqueous mixture of the gelatin and (ii) adding a second polymer component to the aqueous mixture of loading substance and gelatin.

63. The process of claim 50, wherein the pH in step (b) is adjusted to a value from 3.5 to 5.0.

64. The process of claim 50, wherein the pH in step (b) is adjusted to a value from 4.0 to 5.0.

65. The process of claim 50, wherein the temperature is initially from about 20° C. to about 60° C.

66. The process of claim 50, wherein the mixture in step (c) is cooled at a rate of 1° C./10 minutes.

67. The process of claim 50, wherein the mixture in step (c) is cooled until it reaches a temperature of from about 3° C. to about 10° C.

68. The process of claim 51, further comprising adding a cross-linker to cross-link the gelatin and second polymer component.

69. The process of claim 51, further comprising after step (d) adding a cross-linker to cross-link the gelatin and second polymer component.

70. The process of claim 68, wherein the cross-linker comprises an enzymatic cross-linker, an aldehyde, tannic acid, alum, a plant extract, a phenolic compound, or a mixture thereof.

71. The process of claim 68 wherein the cross-linker is gluteraldehyde.

72. The process of claim 68, wherein the cross-linker is transglutaminase.

73. The process of claim 50, further comprising drying the microcapsule after step (d).

74. The process of claim 50, further comprising after step (d), mixing the microcapsule with a third polymer component and adjusting the pH, temperature, concentration, mixing speed or a combination thereof to form a shell material comprising the third polymer component, wherein third polymer component forms a shell around microcapsule.

75. A process for preparing microcapsules, the process comprising:
    (a) providing an emulsion comprising a loading substance and a gelatin having a Bloom number less than 50; and
    (b) drying the emulsion to produce the microcapsules.

76. The process of claim 75, wherein the drying step comprises spray drying, freeze drying, fluidized bed drying, or drum drying.

77. The process of claim 75, wherein the drying step comprises spray drying.

78. A microcapsule produced by the process of claim 50.

79. A microcapsule produced by the process of claim 75.

80. A foodstuff comprising the microcapsule of claim 1.

81. The foodstuff of claim 80, wherein the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar, a sauce, a gravy, a syrup, a nutritional bar, a beverage, a dry beverage powder, a jam or jelly, a fish product, or pet companion food.

82. The foodstuff of claim 80, wherein the foodstuff is bread, tortillas, cereal, sausage, chicken, ice cream, yogurt, milk, salad dressing, rice bran, fruit juice, a dry beverage powder, rolls, cookies, crackers, fruit pies, or cakes.

83. A foodstuff comprising the microcapsule of claim 1.

84. The foodstuff of claim 83, wherein the foodstuff is kosher or Halal.

85. A foodstuff comprising the microcapsule of claim 34.

86. The foodstuff of claim 85, wherein the foodstuff is kosher or Halal.

87. A foodstuff comprising the microcapsule of claim 78.

88. The foodstuff of claim 87, wherein the foodstuff is kosher or Halal.

89. A foodstuff comprising the emulsion of claim 45.

90. The foodstuff of claim 89, wherein the foodstuff is kosher or Halal.

91. A pharmaceutical formulation comprising the microcapsule of claim 1 and a pharmaceutically acceptable carrier.

92. A pharmaceutical formulation comprising the microcapsule of claim 34 and a pharmaceutically acceptable carrier.

93. A pharmaceutical formulation comprising the microcapsule of claim 78 and a pharmaceutically acceptable carrier.

94. A pharmaceutical formulation comprising the emulsion of claim 45 and a pharmaceutically acceptable carrier.

95. A method for delivering a loading substance to a subject, comprising administering to the subject the microcapsule of claim 1.

96. The method of claim 95, wherein the subject is a mammal.

97. The method of claim 95, wherein the subject is a human.

98. The method of claim 95, wherein the subject is a domesticated animal.

99. The method of claim 95, wherein the subject is a mice, a rat, a cow, a horse, a sheep, a goat, a primate, a fish, a shellfish, a crustacean, a bird, a dog, or a cat.

100. A method for delivering a loading substance to a subject, comprising administering to the subject the microcapsule of claim 34.

101. A method for delivering a loading substance to a subject, comprising administering to the subject the microcapsule of claim 78.

102. A method for delivering a loading substance to a subject, comprising administering to the subject the emulsion of claim 45.

103. A method for stabilizing an emulsion, comprising admixing an aqueous mixture of a loading substance with a gelatin having a Bloom number less than 50.

* * * * *

UNITED STATES PATENT AND TRADEMARK OFFICE
CERTIFICATE OF CORRECTION

| | | |
|---|---|---|
| PATENT NO. | : 6,969,530 B1 | |
| APPLICATION NO. | : 11/040820 | |
| DATED | : November 29, 2005 | |
| INVENTOR(S) | : Curtis et al. | |

It is certified that error appears in the above-identified patent and that said Letters Patent is hereby corrected as shown below:

Title Page
    On page 1 of the issued patent, in the section labeled, "Inventors", please include the following name as a co-inventor along with "Jonathan Michael Curtis, Wei Zhang and Yulai Jin":

-- Colin James Barrow, Halifax (CA) --

Signed and Sealed this

Twelfth Day of December, 2006

JON W. DUDAS
*Director of the United States Patent and Trademark Office*